US006482600B1

(12) United States Patent
Burmer et al.

(10) Patent No.: US 6,482,600 B1
(45) Date of Patent: Nov. 19, 2002

(54) BREAST CANCER ASSOCIATED NUCLEIC ACID SEQUENCES AND THEIR ASSOCIATED PROTEINS

(75) Inventors: Glenna C. Burmer, Seattle, WA (US); Joseph P. Brown, Seattle, WA (US); Amanda A. Ford, Carnation, WA (US)

(73) Assignee: LifeSpan BioSciences, Inc., Seattle, WA (US)

( * ) Notice: Subject to any disclaimer, the term of this patent is extended or adjusted under 35 U.S.C. 154(b) by 0 days.

(21) Appl. No.: 09/306,564

(22) Filed: May 6, 1999

Related U.S. Application Data

(60) Provisional application No. 60/084,599, filed on May 7, 1998.

(51) Int. Cl.$^{7}$ .............................................. G01M 33/53

(52) U.S. Cl. .................... 435/7.23; 435/7.92; 435/7.93; 435/7.94; 435/7.95; 435/960; 435/962; 530/387.1; 530/350

(58) Field of Search ............................... 435/7.23, 7.92, 435/7.93, 7.94, 7.95, 960, 962; 530/387.1, 350

(56) References Cited

U.S. PATENT DOCUMENTS 5,776,676 A 7/1998 Prasad et al. .................. 435/6

OTHER PUBLICATIONS

Alberts, Mol. Biol. Cell, 3$^{rd}$ ed. p. 465, 1994.*

Shautz, Intl. J. Biochem & Cell Biol. 31: 107–122, 1999.*

McClean, Eur. J. Cancer 29A: 2243–2248, 1993.*

Fr. EMBO J. 15: 4392–4401, 1996.*

Muratake et al, Accession No. 580794, Gen Bank and MPSRCH Search Report, p. 5, 1996.*

Greenspan, Nature Biotechnology 7:936–937, 1999.*

JP 0 2 111 796A—Accession No.: R 05084. Gen Bank and MPSRCH Search Report p. 1–2, 1990.*

Gross R. Accession No: R 47556, Gen Bank, 1994.*

Ichimura–Ohshima et al., "cDNA Cloning and Chromosome Assignment of the Gene for Human Brain 14–3–3 Protein n Chain," *Journal of Neuroscience Research* (1992) 31: 600–605.

Muratake et al., "Structural Organization and Chromosomal Assignment of the Human 14–3–3 n Chain Gene (YWHAH)," *Genomics* (1996) 36: 63–69.

Nakanishi et al., "Elevated Expression Levels of the 14–3–3 Family of Proteins in Lung Cancer Tissues," *Human Antibodies* (1997) 8(4): 189–194.

Setoguchi et al., "Immunocytochemical Detection of Lung Cancer Cells with Monoclonal Antibodies to 14–3–3 Proteins," *Hum. Antibod. Hybridomas*(1995) 6(4): 137–144.

* cited by examiner

*Primary Examiner*—Susan Ungar
*Assistant Examiner*—Minh Tam Davis
(74) *Attorney, Agent, or Firm*—Townsend and Townsend and Crew LLP

(57) ABSTRACT

This invention relates to the discovery of the association of certain nucleic acid sequences and proteins with breast cancer, the use of such sequences as a diagnostic indicator and treatments based on the association.

7 Claims, No Drawings

BREAST CANCER ASSOCIATED NUCLEIC ACID SEQUENCES AND THEIR ASSOCIATED PROTEINS

CROSS-REFERENCE TO RELATED APPLICATIONS

This application claims the benefit of U.S. Provisional Patent Application Ser. No. 60/084,599, filed May 7, 1998, which is incorporated herein by reference in its entirety for all purposes.

GOVERNMENT RIGHTS

Not applicable.

FIELD OF THE INVENTION

This invention relates to the discovery of the association of certain nucleic acid sequences and proteins with breast cancer. The identification of these breast cancer-associated nucleic acid sequences and proteins have diagnostic uses in detecting the breast cancer status of a cell population as well as application for therapy of breast cancer.

BACKGROUND OF THE INVENTION

Breast cancer is a major affliction of women in developed countries. It is estimated in the United States, for example, that 12 percent of all women will be given a diagnosis of breast cancer and 3.5 percent will die of the disease. The incidence rates of the disease increase as women enter their fourth decade of life such that breast cancer is the leading cause of death for women aged 40–55. Though incidence of the disease is high, early diagnosis is key for the long-term survival of a patient afflicted with the disease. Additional methods which will aid in the early diagnosis of the disease and provide a better understanding of it are sorely needed.

SUMMARY OF THE INVENTION

This invention provides for isolated nucleic acid sequences and proteins whose overexpression is associated with breast cancer. Overexpression of any of the subject proteins is indicative of the disease. Methods and materials for detection of such overexpression are described. The invention has application to primary and advanced or metastatic breast cancer. The invention also embraces the use of screening assays for identifying useful pharmaceutical agents, antisense methods for studying breast cancer in animals and cells and therapeutic methods for inhibiting the growth of breast cancer tumor cells.

DEFINITIONS

"Amplification" primers are oligonucleotides comprising either natural or analog nucleotides that can serve as the basis for the amplification of a select nucleic acid sequence. They include both polymerase chain reaction primers and ligase chain reaction oligonucleotides.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, *Fundamental Immunology*, Third Edition, W. E. Paul, ed., Raven Press, N.Y. 1993). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

"Associated" in the context of breast cancer refers to a relationship of the relevant nucleic acid sequences and their overexpression of the subject protein in a cell as an indicator that the cell is a breast cancer cell.

"Biological samples" refers to any tissue or liquid sample having genomic DNA or other nucleic acids (e.g., mRNA) or proteins. It includes both cells with a normal complement of chromosomes and cells suspected of breast cancer.

The term "gene" means the segment of DNA involved in producing a polypeptide chain; it includes regions preceding and following the coding region (leader and trailer) as well as intervening sequences (introns) between individual coding segments (exons).

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

As used herein a "nucleic acid probe" is defined as a nucleic acid capable of binding to a target nucleic acid (e.g., a nucleic acid associated with breast cancer) of complementary sequence through one or more types of chemical bonds, usually through complementary base pairing, usually through hydrogen bond formation. As used herein, a probe may include natural (i.e. A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions.

Nucleic acid probes can be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981) (Beaucage and Carruthers), or by the triester method according to Matteucci, et al., *J. Am. Chem. Soc.*, 103:3185 (1981) (Matteucci), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

A "labeled nucleic acid probe" is a nucleic acid probe that is bound, either covalently, through a linker, or through ionic, van der Waals or hydrogen bonds to a label such that the presence of the probe may be detected by detecting the presence of the label bound to the probe.

The term "target nucleic acid" refers to a nucleic acid (often derived from a biological sample), to which a nucleic acid probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

The phrase "a nucleic acid sequence encoding" refers to a nucleic acid which contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

"Overexpression" of a protein refers to an event where a gene is expressed multiple times by a single cell or cell population to produce multiple copies of protein. Overexpression may be measured as explained below.

"Proliferating cells" are those which are actively undergoing cell division and grow exponentially.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>O) and N (penalty score for mismatching residues; always<O). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nattl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays," Elsevier, New York. Generally, highly stringent hybridization and wash conditions are selected to be about 5n C lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42 nC, with the hybridization being carried out overnight. An example of highly stringent wash conditions is 0.15M NaCl at 72 nC for about 15 minutes. An example of stringent wash conditions is a 0.2×SSC wash at 65 nC for 15 minutes (see, Sambrook, supra., for a description of SSC buffer). Often, a high stringency wash is preceded by a low stringency wash to remove background probe signal. An example medium stringency wash for a duplex of, e.g., more than 100 nucleotides, is 1×SSC at 45 nC for 15 minutes. An example low stringency wash for a duplex of, e.g., more than 100 nucleotides, is 4–6×SSC at 40 nC for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30 nC. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A further indication that two nucleic acid sequences or polypeptides are substantially identical is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the polynucleotides of the invention can be selected to obtain antibodies specifically immunoreactive with that protein and not with other proteins except for polymorphic variants. For example, polyclonal antibodies raised to one of the BCAS proteins can be selected to obtain only those polyclonal antibodies that are specifically immunoreactive with such protein and not with other proteins, except for polymorphic variants and alleles of the BCAS protein of interest. Typically a specific or selective reaction will be at least twice background signal or noise and more typically more than 10 to 100 times background. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

A "conservative substitution", when describing a protein refers to a change in the amino acid composition of the protein that does not substantially alter the proteints activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following is six groups each containing amino acids that are examples of conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) *Proteins*, W. H. Freeman and Company. In addition, individual substitutions, deletions or additions which alter, add or delete a single amino acid or a small percentage of amino acids in an encoded sequence are also "conservatively modified variations".

A "subsequence" refers to a sequence of nucleic acids or amino acids that comprise a part of a longer sequence of nucleic acids or amino acids (e.g., polypeptide) respectively.

DETAILED DESCRIPTION

This invention relates to the surprising discovery that overexpression of certain proteins are associated with and indicative of breast cancer. Host cells, vectors, probes and primers are described, as are antibodies to the proteins. The description below teaches how to obtain the nucleic acid sequences and their genes, how to express and purify the gene product and describe various methods one could use to detect and quantify the expression and quality of the proteins and uses for them.

We have found that proteins encoded by specific sequences are overexpressed in breast cancer cell populations. These sequences are wholly or partially known and are set out below with reference to their GenBank Accession No. The BCAS sequences include those sequences that encode a protein which specifically binds to polyclonal antibodies raised against a protein encoded by a sequence comprising a sequence selected from the group consisting of SEQ ID NOS: 1–5. The BCAS sequences also include those that are conservatively modified sequences thereof and those that are substantially identical to SEQ ID NOS: 1–5 (all such sequences are referred to herein as breast-cancer associated sequences "BCAS").

| IMAGE CONSORTIUM NO. CLONE ID | GENBANK ACCESSION NO. | GENE DESCRIPTION |
|---|---|---|
| 31183 | R17530 (SEQ ID NO: 1) | Unidentified |
| 42851 | R61133 (SEQ ID NO: 2) | Unidentified |
| 110966 | T83032 (SEQ ID NO: 3) | HsCdc18p (human, 392 nt, 94%) |
| 150267 | H00694 (SEQ ID NO: 4) | Chorionic gonadotropin (human, 319 nt, 99%) |
| 685991 | AA256774 (SEQ ID NO: 5) | 14-3-3 protein eta chain (human, 402 nt, 100%) |

I. Overexpression of the BCAS Proteins

We have determined that the proteins encoded by the BCAS are overexpressed in breast cancer cell populations. The proteins are expressed at lower levels in normal human cells.

Overexpression of the BCAS proteins, can be determined by any method known and available in the art, including methods which indicate that the protein has been specifically expressed even though the protein itself or the entire protein may not have been isolated. Overexpression is indicated if the presence of the protein is greater than 3-fold, preferably greater than 5-fold, and most preferably greater than 10-fold that in a normal human breast cell. For example, mRNA (messenger RNA) copies of the gene of interest can be detected from a suspect cell population and the relative concentrations compared with a control cell population through a Northern blot process, reverse transcriptase PCR, a cDNA Southern blot process and the like.

Antibodies specifically immunoreactive with the BCAS proteins, can be used to identify and quantify the protein in a suspect biological cell sample. Monoclonal antibodies or recombinant forms thereof specifically immunoreactive with one of the BCAS proteins, may be produced by any method known in the art and are claimed here. The use of all antibodies specifically immunoreactive with one of the BCAS proteins, including polyclonal antibodies, in a method to detect for breast cancer is also an aspect of this invention.

This invention and its methods rely in part on routine techniques in the field of recombinant genetics. A basic text disclosing the general methods of use in this invention is Sambrook et al., *Molecular Cloning, A Laboratory Manual*, Cold Spring Harbor Publish., Cold Spring Harbor, N.Y. 2nd ed. (1989) and Kriegler, *Gene Transfer and Expression: A Laboratory Manual*, W. H. Freeman, N.Y., (1990), which are both incorporated herein by reference. Unless otherwise stated all enzymes are used in accordance with the manufacturer's instructions.

Nucleotide sizes are given in either kilobases (Kb) or base pairs (bp). These are estimates derived from agarose or acrylamide gel electrophoresis or from published DNA sequences.

Oligonucleotides that are not commercially available can be chemically synthesized according to the solid phase phosphoramidite triester method first described by S. L. Beaucage and M. H. Caruthers, *Tetrahedron Letts*., 22(20) :1859–1862 (1981), using an automated synthesizer, as described in D. R. Needham Van Devanter et. al., *Nucleic Acids Res*., 12:61 59–6168, (1984). Purification of oligonucleotides is by either native acrylamide gel electrophoresis or by anion-exchange HPLC as described in J. D. Pearson and F. E. Reanier, *J. Chrom*., 255:137–149, (1983).

The nucleic acid sequences described here, or fragments thereof, can be used as a hybridization probe for a cDNA library to isolate the corresponding full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons and introns. An example of such screen includes isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The sequence of the cloned genes and synthetic oligonucleotides can be verified using the chemical degradation method of A. M. Maxam et al., *Methods in Enzymology*, 65:499560, (1980). The sequence can be confirmed after the assembly of the oligonucleotide fragments into the double-stranded DNA sequence using the method of Maxam and Gilbert, supra, or the chain termination method for sequencing double-stranded templates of R. B. Wallace et al., *Gene*, 16:21–26, (1981). Southern blot hybridization techniques can be carried out according to Southern et al., *J. Mol. Biol.*, 98:503, (1975).

II. Cloning Methods for the Isolation of Nucleotide Sequences Encoding The Desired Proteins In general, the nucleic acid sequences encoding the subject proteins are cloned from DNA sequence libraries that are made to encode copy DNA (cDNA) or genomic DNA. The particular sequences can be located by hybridizing with an oligonucleotide probe, the sequence of which can be derived from the sequence listing provided herein, which provides a reference for PCR primers and defines suitable regions for isolating BCAS—specific probes. Alternatively, where the sequence is cloned into an expression library, the expressed recombinant protein can be detected immunologically with antisera or purified antibodies made against BCAS protein.

To make the cDNA library, one should choose a source that is rich in mRNA. The mRNA can then be made into cDNA, ligated into a recombinant vector, and transfected into a recombinant host for propagation, screening and cloning. Methods for making and screening cDNA libraries are well known. See Gubler, U. and Hoffman, B. J. *Gene* 25:263–269, (1983) and Sambrook, supra.

For a genomic library, the DNA is extracted from the tissue and either mechanically sheared or enzymatically digested to yield fragments of preferably about 5–100 kb. The fragments are then separated by gradient centrifugation from undesired sizes and are constructed in bacteriophage lambda vectors. These vectors and phage are packaged in vitro, as described in Sambrook. Recombinant phage are analyzed by plaque hybridization as described in Benton and Davis, *Science*, 196:180–182 (1977). Colony hybridization is carried out as generally described in M. Grunstein et al. *Proc. Natl. Acad. Sci. USA*., 72:3961–3965 (1975).

An alternative method combines the use of synthetic oligonucleotide primers with polymerase extension on an mRNA or DNA template. This polymerase chain reaction (PCR) method amplifies nucleic acid sequences of the protein directly from mRNA, from cDNA, from genomic libraries or cDNA libraries. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of BCAS encoding mRNA in physiological samples, for nucleic acid sequencing, or for other purposes. U.S. Pat. Nos. 4,683,195 and 4,683,202 describe this method. Genes amplified by the PCR reaction can be purified from agarose gels and cloned into an appropriate vector.

Synthetic oligonucleotides can be used to construct genes. This is done using a series of overlapping oligonucleotides, usually 40–120 bp in length, representing both the sense and nonsense strands of the gene. These DNA fragments are then annealed, ligated and cloned.

The BCAS genes for example, may be cloned using intermediate vectors before transformation into mammalian cells for expression. These intermediate vectors are typically prokaryote vectors or shuttle vectors. The proteins can be expressed in either prokaryotes or eukaryotes.

A. Expression in Prokaryotes

To obtain high level expression of a cloned gene, such as those cDNAs encoding BCAS-related proteins in a prokaryotic system, it is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., *J. Bacteriol.*, 158:1018–1024 (1984), and the leftward promoter of phage lambda ($P_L$) as described by Herskowitz, I. and Hagen, D., *Ann. Rev. Genet.*, 14:399–445 (1980).

B. Expression in Eukaryotes

Standard eukaryotic transfection methods are used to produce mammalian, yeast or insect cell lines which express large quantities of the desired protein which are then purified using standard techniques. See, e.g., Colley et al., *J. Biol. Chem.* 264:17619–17622, (1989), and Guide to Protein Purification, in Vol. 182 of *Methods in Enzymology* (Deutscher ed., 1990), both of which are incorporated herein by reference.

Transformations of eukaryotic cells are performed according to standard techniques as described by D. A. Morrison, *J. Bact.*, 132:349–351 (1977), or by J. E. Clark-Curtiss and R. Curtiss, *Methods in Enzymology*, 101:347–362, Eds. R. Wu et. al., Academic Press, New York (1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see Sambrook et al., supra). It is only necessary that the particular genetic engineering procedure utilized be capable of successfully introducing at least one gene into the host cell which is capable of expressing the protein.

The particular eukaryotic expression vector used to transport the genetic information into the cell is not particularly critical. Any of the conventional vectors used for expression in eukaryotic cells may be used. Expression vectors containing regulatory elements from eukaryotic viruses are typically used. SV40 vectors include pSVT7 and pMT2. Vectors derived from bovine papilloma virus include pBV-1 MTHA, and vectors derived from Epstein Bar virus include pHEBO, and p205. Other exemplary vectors include pMSG, pAV009/$A^+$, pMTO10/$A^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors usually include selectable markers which result in gene amplification such as thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with a target protein encoding sequence under the direction of the polyhedrin promoter or other strong baculovirus promoters.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see Sambrook et al., supra, Ch. 16.

The prokaryotic elements that are typically included in the mammalian expression vector include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, and any of the many resistance genes known in the art are suitable. The prokaryotic sequences are preferably chosen such that they do not interfere with the replication of the DNA in eukaryotic cells.

The expression vector contains a eukaryotic transcription unit or expression cassette that contains all the elements required for the expression of the BCAS protein encoding DNA in eukaryotic cells. A typical expression cassette contains a promoter operably linked to the DNA sequence encoding the BCAS protein and signals required for efficient polyadenylation of the transcript. The DNA sequence encoding the protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression*, Cold Spring Harbor Pres, Cold Spring Harbor, N.Y. 1983, which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

1. Expression in Yeast.

Synthesis of heterologous proteins in yeast is well known and described. *Methods in Yeast Genetics*, Sherman, F., et al., Cold Spring Harbor Laboratory, (1982) is a well recognized work describing the various methods available to produce protein in yeast.

For high level expression of a gene in yeast, it is essential to connect the gene to a strong promoter system as in the prokaryote and also to provide efficient transcription termination/polyadenylation sequences from a yeast gene. Examples of useful promoters include GALI, IO (Johnson, M., and Davies, R. W., *Mol. and Cell. Biol.*, 4:1440–1448 (1984)) ADH2 (Russell, D., et al., *J. Biol. Chem.*, 258:2674–2682, (1983)), PH05 (*EMBO J.* 6:675–680, (1982)), and MFrI. A multicopy plasmid with a selective marker such as Leu-2, URA-3, Trp-I, and His-3 is also desirable.

The MFrI promoter is preferred for expression of the subject protein in yeast. The MFrI promoter, in a host of the r mating-type is constitutive, but is switched off in diploids or cells with the a mating-type. It can, however, be regulated by raising or lowering the temperature in hosts which have a ts mutation at one of the SIR loci. The effect of such a mutation at 35 nC on an r type cell is to turn on the normally silent gene coding for the r mating-type. The expression of the silent a mating-type gene, in turn, turns off the MFrI promoter. Lowering the temperature of growth to 27 nC reverses the whole process, i.e., turns the a mating-type off and turns the MFrI on (Herskowitz, I. and Oshima, Y., in *The Molecular Biology of the Yeast Saccharomyces*, (eds. Strathern, J. N. Jones, E. W., and Broach, J. R., Cold Spring Harbor Lab., Cold Spring Harbor, N.Y., pp.181–209, (1982).

The polyadenylation sequences are provided by the 3'-end sequences of any of the highly expressed genes, like ADHI, MFr1, or TPI (Alber, T. and Kawasaki, G., *J. of Mol. & Appl. Genet.* 1:419–434, (1982).

A number of yeast expression plasmids like YEp6, YEpI3, YEp4 can be used as vectors. A gene of interest can be fused to any of the promoters in various yeast vectors. The above-mentioned plasmids have been fully described in the literature *Botstein, etal.*, 1979, *Gene*, 8:17–24, (1979); Broach, et al., *Gene*, 8:121–133, (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, *Nature* (London), 275:104–109, (1978); and Hinnen, A., et al., *Proc. Natl. Acad. Sci. USA*, 75:1929–1933, (1978). The second procedure does not involve removal of the cell wall. Instead the cells are treated with lithium chloride or acetate and PEG and put on selective plates (Ito, H., et al., *J. Bact.*, 153:163–168, (1983)).

The protein can be isolated from yeast by lysing the cells and applying standard protein isolation techniques to the lysates. The monitoring of the purification process can be accomplished by using Western blot techniques or radioimmunoassays.

2. Expression in Insect Cells.

The baculovirus expression vector utilizes the highly expressed and regulated *Autographa californica* nuclear polyhedrosis virus (AcMNPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically, and functionally similar to their natural counterparts. In addition, the baculovirus vector utilizes many of the protein modification, processing, and transport systems that occur in higher eukaryotic cells.

Briefly, the DNA sequence encoding the subject protein is inserted into a transfer plasmid vector in the proper orientation downstream from the polyhedrin promoter, and flanked on both ends with baculovirus sequences. Cultured insect cell, commonly *Spodoptera frugiperda*, are transfected with a mixture of viral and plasmid DNAs. The virus that develop, some of which are recombinant virus that result from homologous recombination between the two DNAs, are plated at 100–1000 plaques per plate. The plaques containing recombinant virus can be identified visually because of their ability to form occlusion bodies or by DNA hybridization. The recombinant virus is isolated by plague purification. The resulting recombinant virus, capable of expressing the subject protein, is self propagating in that no helper virus is required for maintenance or replication. After infecting an insect culture with recombinant virus, one can expect to find recombinant protein within 48–72 hours. The infection is essentially lytic within 4–5 days.

There are a variety of transfer vectors into which the nucleotides of the invention can be inserted. For a summary of transfer vectors see Luckow, V. A. and M. D. Summers, *Bio/Technology*, 6:47–55 (1988). Preferred is the transfer vector pAcUW21 described by Bishop, D. H. L. in *Seminars in Virology*, 3:253–264, (1992).

3. Expression in Recombinant Vaccinia Virus-infected Cells.

The gene encoding BCAS protein is inserted into a plasmid designed for producing recombinant vaccinia, such as pGS62, Langford, C. L., et al., *Mol. Cell. Biol.* 6:3191–3199, (1986). This plasmid consists of a cloning site for insertion of foreign genes, the P7.5 promoter of vaccinia to direct synthesis of the inserted gene, and the vaccinia TK gene flanking both ends of the foreign gene.

When the plasmid containing the desired nucleotide sequence is constructed, the gene can be transferred to vaccinia virus by homologous recombination in the infected cell. To achieve this, suitable recipient cells are transfected with the recombinant plasmid by standard calcium phosphate precipitation techniques into cells already infected with the desirable strain of vaccinia virus, such as Wyeth, Lister, WR or Copenhagen. Homologous recombination occurs between the TK gene in the virus and the flanking TK gene sequences in the plasmid. This results in a recombinant virus with the foreign gene inserted into the viral TK gene, thus rendering the TK gene inactive. Cells containing recombinant viruses are selected by adding medium containing 5-bromodeoxyuridine, which is lethal for cells expressing a TK gene.

Confirmation of production of recombinant virus can be achieved by DNA hybridization using cDNA encoding the BCAS protein and by immunodetection techniques using antibodies specific for the expressed protein. Virus stocks may be prepared by infection of cells such as HeLA S3 spinner cells and harvesting of virus progeny.

4. Expression in Cell Cultures.

The protein cDNA of the invention can be ligated to various expression vectors for use in transforming host cell cultures. The vectors typically contain gene sequences to initiate transcription and translation of the BCAS gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of the BCAS protein. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines. NIH 3T3 or COS cells are preferred.

As indicated above, the vector, e.g., a plasmid, which is used to transform the host cell, preferably contains DNA sequences to initiate transcription and sequences to control the translation of the subject protein gene sequence. These sequences are referred to as expression control sequences. Illustrative expression control sequences are obtained from the SV-40 promoter (*Science*, 222:524–527, (1983)), the CMV I.E. Promoter (*Proc. Natl. Acad. Sci.* 81:659–663, (1984)) or the metallothionein promoter (*Nature* 296:39–42, (1982)). The cloning vector containing the expression control sequences is cleaved using restriction enzymes and adjusted in size as necessary or desirable and ligated with sequences encoding the desired protein by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., *J. Virol.* 45: 773–781, (1983)).

Additionally, gene sequences to control replication in the host cell may be incorporated into the vector such as those found in bovine papilloma virus type-vectors. Saveria-Campo, M., "*Bovine Papilloma virus DNA a Eukaryotic Cloning Vector*" in DNA Cloning Vol. II a Practical Approach Ed. D. M. Glover, IRL Press, Arlington, Va. pp. 213–238, (1985).

The transformed cells are cultured by means well known in the art. For example, as published in *Biochemical Methods in Cell Culture and Virology*, Kuchler, R. J., Dowden, Hutchinson and Ross, Inc., (1977). The expressed G-6-Pase protein is isolated from cells grown as suspensions or as monolayers. The latter are recovered by well known mechanical, chemical or enzymatic means.

III. Detection and Genomic Analysis of BCAS Proteins and Nucleic Acids

The polynucleotides and polypeptides of the present invention can be employed as research reagents and materials for discovery of treatments and diagnostics to human disease.

As should be apparent to those of skill in the art, the invention is the identification of BCAS genes and the discovery that overexpression of certain BCAS sequences are associated with breast cancer. Accordingly, the present invention also includes methods for detecting the presence, alteration or absence of the such associated DNA or RNA in a physiological specimen in order to determine tumorigenicity of breast cells. Although any tissue having cells bearing the genome of an individual, or RNA associated with breast cancer, can be used, the most convenient specimen will be blood samples or biopsies of suspect tissue. It is also possible and preferred in some circumstances to conduct assays on cells that are isolated under microscopic visualization. A particularly useful method is the microdissection technique described in PCT application WO/95/23960. The cells isolated by microscopic visualization can be used in any of the assays described herein including both genomic and immunologic based assays.

A. Detection of Target DNA and Overexpression Using RNA

The invention provides methods for detecting whether a cell is tumorigenic. The methods typically comprise contacting RNA from the cell with a probe which comprises a polynucleotide sequence associated with breast cancer, and determining whether the amount of said probe which hybridizes to the RNA is increased or decreased relative to the amount of said probe which hybridizes to RNA from a non-tumorigenic cell.

The probes are capable of binding to a target nucleic acid (e.g., a nucleic acid associated with tumorigenicity). By assaying for the presence or absence of the probe, one can detect the presence or absence of the target nucleic acid in a sample. Preferably, non-hybridizing probe and target nucleic acids are removed (e.g., by washing) prior to detecting the presence of the probe.

A variety of methods of specific DNA and RNA measurement using nucleic acid hybridization techniques are known to those of skill in the art. See Sambrook. For example, one method for evaluating the presence or absence of the DNA in a sample involves a Southern transfer. Briefly, the digested genomic DNA is run on agarose slab gels in buffer and transferred to membranes. Hybridization is carried out using the probes discussed above. Visualization of the hybridized portions allows the qualitative determination of the presence, alteration or absence of a BCAS gene.

A northern transfer may be used for the detection of breast cancer-associated mRNA in samples of RNA from cells expressing the proteins. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with a Southern blot, labeled probes are used to identify the presence or absence of the subject protein transcript.

The selection of a nucleic acid hybridization format is not critical. A variety of nucleic acid hybridization formats are known to those skilled in the art. For example, common formats include sandwich assays and competition or displacement assays. Hybridization techniques are generally described in "*Nucleic Acid Hybridization, A Practical Approach*," Ed. Hames, B. D. and Higgins, S. J., IRL Press, 1985; Gall and Pardue (1969), *Proc. Natl. Acad. Sci., U.S.A*., 63:378–383; and John, Burnsteil and Jones (1969) *Nature*, 223:582–587.

For example, sandwich assays are commercially useful hybridization assays for detecting or isolating nucleic acid sequences. Such assays utilize a "capture" nucleic acid covalently immobilized to a solid support and labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

It will be appreciated that nucleic acid hybridization assays can also be performed in an array-based format as described in Fodor et al. (1991) Science, 251: 767–777; Sheldon et al. (1993) Clinical Chemistry 39(4): 718–719, and Kozal et al. (1996) *Nature Medicine* 2(7): 753–759. In this approach, arrays bearing a multiplicity of different "probe" nucleic acids (usually amplified DNA) are hybridized against a target nucleic acid. In this manner a large number of different hybridization reactions can be run essentially "in parallel". This provides rapid, essentially simultaneous, evaluation of a wide number of reactants. Methods of performing hybridization reactions in array based formats are well known to those of skill in the art (see, e.g., Jackson et al. (1996) *Nature Biotechnology*, 14: 1685–1691, and Chee et al. (1995) *Science*, 274: 610–613).

The probes are typically labeled directly, as with isotopes, chromophores, lumiphores, chromogens, or indirectly labeled such as with biotin to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^{3}H$, $_{125}I$, $_{35}S$, $^{14}C$, or $^{32}P$-labelled probes or the like.

Other labels include ligands which bind to labelled antibodies, fluorophores, chemiluminescent agents, enzymes, and antibodies which can serve as specific binding pair members for a labelled ligand. An introduction to labels, labeling procedures and detection of labels is found in Polak and Van Noorden (1997) *Introduction to Immunocytochemistry*, 2nd ed., Springer Verlag, N.Y. and in Haugland (1996) *Handbook of Fluorescent Probes and Research Chemicals*, a combined handbook and catalogue Published by Molecular Probes, Inc., Eugene, Oreg. Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green , rhodamine and derivatives (e.g., Texas red, tetrarhodimine isothiocynate (TRITC), etc.), digoxigenin, biotin, phycoerythrin, AMCA, CyDyes, and the like), radiolabels (e.g., $^{3}H$, $_{125}I$, $_{35}S$, $^{14}C$, $^{32}P$, $^{33}P$, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label may be coupled directly or indirectly to a component of the detection assay (e.g., the probe) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/ Gibco BRL; 2) color production (using both horseradish peroxidase and/or alkaline phosphatase with substrates that produce a colored precipitate [kits available from Life Technologies/Gibco BRL, and Boehringer-Mannheim]); 3) hemifluorescence using, e.g., alkaline phosphatase and the substrate AttoPhos [Amersham] or other substrates that produce fluorescent products, 4) fluorescence (e.g., using Cy-5 [Amersham]), fluorescein, and other fluorescent tags]; 5) radioactivity. Other methods for labeling and detection will be readily apparent to one skilled in the art.

Preferred enzymes that can be conjugated to detection reagents of the invention include, e.g., t-galactosidase, luciferase, horse radish peroxidase, and alkaline phosphatase. The chemiluminescent substrate for luciferase is luciferin. One embodiment of a chemiluminescent substrate for t-galactosidase is 4-methylumbelliferyl-t-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[ 1,2-dioxetane-3, 2'-adamantane], which is detected with a luminometer. Embodiments of horse radish peroxidase substrates include 2,2' azino-bis(3-ethylbenzthiazoline-6 sulfonic acid) (ABTS), 5-aminosalicylic acid (5AS), o-dianisidine, and o-phenylenediamine (OPD), which are detected with a spectrophotometer; and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

Most typically, the amount of a BCAS-associated RNA is measured by quantitating the amount of label fixed to the solid support by binding of the detection reagent. Typically, presence of a modulator during incubation will increase or decrease the amount of label fixed to the solid support relative to a control incubation which does not comprise the modulator, or as compared to a baseline established for a particular reaction type. Means of detecting and quantitating labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement. Exemplar solid supports include glasses, plastics, polymers, metals, metalloids, ceramics, organics, etc. Solid supports can be flat or planar, or can have substantially different conformations. For example, the substrate can exist as particles, beads, strands, precipitates, gels, sheets, tubing, spheres, containers, capillaries, pads, slices, films, plates, dipsticks, slides, etc. Magnetic beads or particles, such as magnetic latex beads and iron oxide particles, are examples of solid substrates that can be used in the methods of the invention. Magnetic particles are described in, for example, U.S. Pat. No. 4,672,040, and are commercially available from, for example, PerSeptive Biosystems, Inc. (Framingham Mass.), Ciba Corning (Medfield Mass.), Bangs Laboratories (Carmel Ind.), and BioQuest, Inc. (Atkinson N.H.). The substrate is chosen to maximize signal to noise ratios, primarily to minimize background binding, for ease of washing and cost.

A variety of automated solid-phase assay techniques are also appropriate. For instance, very large scale immobilized polymer arrays (VLSIPS™), available from Affymetrix, Inc. in Santa Clara, Calif. can be used to detect changes in expression levels of a plurality of BCAS-associated nucleic acids simultaneously. See, Tijssen (supra.), Fodor et al. (1991) *Science*, 251: 767–777; Sheldon et al. (1993) *Clinical Chemistry* 39(4): 718–719, and Kozal et al. (1996) *Nature Medicine* 2(7): 753–759. Thus, in one embodiment, the invention provides methods of detecting expression levels of BCAS nucleic acids, in which nucleic acids (e.g., RNA from a cell culture), are hybridized to an array of nucleic acids that are known to be associated with BCAS. For example, in the assay described supra, oligonucleotides which hybridize to a plurality of BCAS nucleic acids are optionally synthesized on a DNA chip (such chips are available from Affymetrix) and the RNA from a biological sample, such as a cell culture, is hybridized to the chip for simultaneous analysis of multiple BCAS nucleic acids. The BCAS nucleic acids that are present in the sample which is assayed are detected at specific positions on the chip.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181:153–162; Bogulavski et al. (1986) *J. Immunol. Methods* 89:123–130; Prooijen-Knegt (1982) *Exp. Cell Res.* 141:397–407; Rudkin (1976) *Nature* 265:472–473, Stollar (1970) *PNAS* 65:993–1000; Ballard (1982) *Mol. Immunol.* 19:793–799; Pisetsky and Caster (1982) *Mol. Immunol.* 19:645–650; Viscidi et al. (1988) *J. Clin. Microbial.* 41:199–209, and Kiney et al. (1989) *J. Clin. Microbiol.* 27:6–12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill can easily make antibodies specific for nucleic acid duplexes using existing techniques, or modify those antibodies which are commercially or publicly available. In addition to the art referenced above, general methods of producing polyclonal and monoclonal antibodies are known to those of skill in the art. See, e.g., Paul (ed) (1993) *Fundamental Immunology*, Third Edition Raven Press, Ltd., New York Coligan (1991) *Current Protocols in Immunology* Wiley/Greene, N.Y.; Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497. Other suitable techniques for antibody preparation include selection of libraries of recombinant antibodies in phage or similar vectors. See, Huse et aL (1989) *Science* 246: 1275–1281; and Ward et al. (1989) *Nature* 341: 544–546. Specific monoclonal and polyclonal antibodies and antisera will usually bind with a $K_D$ of at least about 0.1 $\mu$M, preferably at least about 0.1 $\mu$M or better, and most typically and preferably, 0.001 $\mu$M or better.

The nucleic acid sequences used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may act as a negative probe in an assay sample where only the nucleotide sequence of interest is present.

Typically, labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^{3}$H, $_{125}$I, $^{35}$S, $^{14}$C, or $^{32}$P-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays," *Laboratory Techniques in Biochemistry and Molecular Biology*, Burdon, R. H., van Knippenberg, P. H., Eds., Elsevier (1985), pp. 9–20.)

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

A preferred embodiment is the use of allelic specific amplifications. In the case of PCR, the amplification primers are designed to bind to a portion of the BCAS protein gene but the terminal base at the 3' end is used to discriminate between the mutant and wild-type forms of the BCAS protein gene. If the terminal base matches the point mutation or the wild-type, polymerase dependent three prime extension can proceed and an amplification product is detected. This method for detecting point mutations or polymorphisms is described in detail by Sommer, S. S., et al., in *Mayo Clin. Proc.* 64:1361–1372, (1989), incorporated herein by reference. By using appropriate controls, one can develop a kit having both positive and negative amplification products. The products can be detected using specific probes or by simply detecting their presence or absence. A variation of the PCR method uses LCR where the point of discrimination, i.e, either the point mutation or the wild-type bases fall between the LCR oligonucleotides. The ligation of the oligonucleotides becomes the means for discriminating between the mutant and wild-type forms of the BCAS protein gene.

B. Detection of Overexpression by Isolation of the Protein

If overexpression is to be determined by isolation of the protein, the protein may be purified by standard techniques, including selective precipitation with such substances as ammonium sulfate; column chromatography, immunopurification methods, and others. See, for instance, R. Scopes, *Protein Purification: Principles and Practice*, Springer-Verlag: New York (1982), U.S. Pat. No. 4,673,641, Ausubel, and Sambrook, incorporated herein by reference.

A number of conventional procedures can be employed when protein is being purified. For example proteins having established molecular adhesion properties can be reversible fused to the subject protein. With the appropriate ligand, the BCAS protein can be selectively adsorbed to a purification column and then freed from the column in a relatively pure form. The fused protein is then removed by enzymatic activity. Finally the BCAS protein could be purified and isolated using immunoaffinity columns.

Standard Protein Separation Techniques For Purifying Protein.

1. Solubility Fractionation

Often as an initial step and if the protein mixture is complex, an initial salt fractionation can separate many of the unwanted host cell proteins (or proteins derived from the cell culture media) from the protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20–30%. This will precipitate the most hydrophobic of proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, this knowledge can be used to isolate the target protein of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The protein will pass through the membrane into the filtrate. The filtrate can then be chromatographed as described below.

3. Column Chromatography

The target protein can also be separated from other proteins on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

An alternative means for determining the level of expression of a gene is in situ hybridization. In situ hybridization assays are well known and are generally described in Angerer, et al., *Methods Enzymol.*, 152:649–660 (1987). In an in situ hybridization assay, cells preferentially bovine lymphocytes, are fixed to a solid support, typically a glass slide. If DNA is to be probed, the cells are denatured with heat or alkali. The cells are then contacted with a hybridization solution at a moderate temperature to permit annealing of specific probes that are labelled. The probes are preferably labelled with radioisotopes or fluorescent reporters.

Immunological Detection of Target Protein

In addition to the detection of the target protein expression using nucleic acid hybridization technology, one can also use immunoassays to detect target protein. Immunoassays can be used to qualitatively or quantitatively analyze the proteins of interest. A general overview of the applicable technology can be found in Harlow and Lane, *Antibodies: A Laboratory Manual*, Cold Spring Harbor Pubs., N.Y. (1988), incorporated herein by reference.

1. Antibodies to Breast Cancer-Associated Protein

Methods of producing polyclonal and monoclonal antibodies that react specifically with a protein of interest are known to those of skill in the art. See, e.g., Coligan (1991), CURRENT PROTOCOLS IN IMMUNOLOGY, Wiley/Greene, N.Y.; and Harlow and Lane; Stites et al. (eds.) BASIC AND CLINICAL IMMUNOLOGY (4th ed.) Lange Medical Publications, Los Altos, Calif., and references cited therein; Goding (1986), MONOCLONAL ANTIBODIES: PRINCIPLES AND PRACTICE (2d ed.) Academic Press, New York, N.Y.; and Kohler and Milstein (1975), *Nature*, 256:495–497. Such techniques include antibody preparation by selection of antibodies from libraries of recombinant antibodies in phage or similar vectors. See, Huse et al. (1989), *Science*, 246:1275–1281; and Ward et al. (1989), *Nature*, 341:544–546. For example, in order to produce antisera for use in an immunoassay, the subject protein or an antigenic fragment thereof, is isolated as described herein. For example, recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen.

Polyclonal sera are collected and titered against the immunogen protein in an immunoassay, for example, a solid phase immunoassay with the immunogen immobilized on a solid support. Polyclonal antisera with a titer of $10_4$ or greater are selected and tested for their cross reactivity against non-target proteins or even other homologous proteins from other organisms, using a competitive binding immunoassay. Specific monoclonal and polyclonal antibodies and antisera will usually bind with a $K_D$ of at least about 0.1 mM, more usually at least about 1 *M, preferably at least about 0.1 $\mu$M or better, and most preferably, 0.1 $\mu$M or better.

A number of proteins of the invention comprising immunogens may be used to produce antibodies specifically or selectively reactive with target protein. Recombinant protein is the preferred immunogen for the production of monoclonal or polyclonal antibodies. Naturally occurring protein may also be used either in pure or impure form. Synthetic peptides made using the protein sequences described herein may also be used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to target protein. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Once breast cancer-associated protein or other target protein specific antibodies are available, the protein can be measured by a variety of immunoassay methods with qualitative and quantitative results available to the clinician. For a review of immunological and immunoassay procedures in general, see *Basic and Clinical Immunology* 7th Edition (D. Stites and A. Terr ed.) 1991. Moreover, the immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," Tijssen; and, Harlow and Lane, each of which is incorporated herein by reference.

Immunoassays to measure target protein in a human sample may use a polyclonal antiserum which was raised to the protein partially encoded by a sequence described herein or a fragment thereof. This antiserum is selected to have low crossreactivity against non-target proteins and any such crossreactivity is removed by immunoabsorption prior to use in the immunoassay.

In order to produce antisera for use in an immunoassay, target protein or a fragment thereof, is isolated as described herein. For example, recombinant protein is produced in a transformed cell line. An inbred strain of mice such as Balb/c is immunized with the protein or a peptide using a standard adjuvant, such as Freund's adjuvant, and a standard mouse immunization protocol. Alternatively, a synthetic peptide derived from the sequences disclosed herein and conjugated to a carrier protein can be used as an immunogen. Polyclonal sera are collected and titered against the immunogen protein in an immunoassay, for example, a solid phase immunoassay with the immunogen immobilized on a solid support. Polyclonal antisera with a titer of $10_4$ or greater are selected and tested for their cross reactivity against non-target proteins, using a competitive binding immunoassay such as the one described in Harlow and Lane, supra, at pages 570–573 and below.

2. Immunological Binding Assays.

In a preferred embodiment, a protein of interest is detected and/or quantified using any of a number of well recognized immunological binding assays (see, e.g., U.S. Pat Nos. . 4,366,241; 4,376,110; 4,517,288; and 4,837,168). For a review of the general immunoassays, see also *Methods in Cell Biology* Volume 37 : *Antibodies in Cell Biology*, Asai, ed. Academic Press, Inc. New York (1993); *Basic and Clinical Immunology* 7th Edition, Stites & Terr, eds. (1991). Immunological binding assays (or immunoassays) typically utilize a "capture agent" to specifically bind to and often immobilize the analyte (in this case the breast cancer associated protein or antigenic subsequence thereof). The capture agent is a moiety that specifically binds to the analyte. In a preferred embodiment, the capture agent is an antibody that specifically binds breast cancer-associated protein. The antibody (e.g., anti-target protein) may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled target protein polypeptide or a labeled anti-breast cancer associated protein antibody. Alternatively, the labeling agent may be a third moiety, such as another antibody, that specifically binds to the antibody/breast cancer-associated protein complex.

In a preferred embodiment, the labeling agent is a second breast cancer-associated protein bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom, et al. (1985) *J. Immunol.*, 135: 2589–2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10 nC to 40 nC.

(a) Non-Competitive Assay Formats.

Immunoassays for detecting subject protein from tissue samples may be either competitive or noncompetitive. Noncompetitive immunoassays are assays in which the amount of captured analyte (in this case the protein) is directly measured. In one preferred "sandwich" assay, for example, the capture agent (anti-target protein antibodies) can be bound directly to a solid substrate where they are immobilized. These immobilized antibodies then capture target protein present in the test sample. Target protein thus immobilized is then bound by a labeling agent, such as a second target protein antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

(b) Competitive Assay Formats.

In competitive assays, the amount of target protein (analyte) present in the sample is measured indirectly by measuring the amount of an added (exogenous) analyte (i.e. the target protein) displaced (or competed away) from a capture agent (anti-target protein antibody) by the analyte present in the sample. In one competitive assay, a known amount of, in this case, the target protein is added to the sample and the sample is then contacted with a capture agent, in this case an antibody that specifically binds to the target protein. The amount of target protein bound to the antibody is inversely proportional to the concentration of target protein present in the sample. In a particularly preferred embodiment, the antibody is immobilized on a solid substrate. The amount of the target protein bound to the antibody may be determined either by measuring the amount of target protein present in a target protein/antibody complex, or alternatively by measuring the amount of remaining uncomplexed protein. The amount of target protein may be detected by providing a labeled target protein molecule.

A hapten inhibition assay is another preferred competitive assay. In this assay a known analyte, in this case the target protein is immobilized on a solid substrate. A known amount of anti-target protein antibody is added to the sample, and the sample is then contacted with the immobilized target. In this case, the amount of anti-target protein antibody bound to the immobilized target protein is inversely proportional to the amount of target protein present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Immunoassays in the competitive binding format can be used for crossreactivity determinations. For example, the protein antigens partially encoded by the sequences described herein can be immobilized to a solid support. Proteins are added to the assay which compete with the binding of the antisera to the immobilized antigen. The ability of the above proteins to compete with the binding of the antisera to the immobilized protein is compared to the protein encoded by any of the sequences described herein. The percent crossreactivity for the above proteins is calculated, using standard calculations. Those antisera with less than 10% crossreactivity with each of the proteins listed above are selected and pooled. The cross-reacting antibodies are optionally removed from the pooled antisera by immunoabsorption with the considered proteins, e.g., distantly related homologues.

The immunoabsorbed and pooled antisera are then used in a competitive binding immunoassay as described above to compare a second protein, thought to be perhaps the protein of this invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

(c) Other Assay Formats.

In a particularly preferred embodiment, Western blot (immunoblot) analysis is used to detect and quantify the presence of target protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target protein. For example, the anti-target protein antibodies specifically bind to the target protein peptides on the solid support. These antibodies may be directly labeled or alternatively may be subsequently detected using labeled antibodies (e.g., labeled sheep anti-mouse antibodies) that specifically bind to the anti-target protein antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34–41).

3. Reduction of Non-Specific Binding.

One of skill in the art will appreciate that it is often desirable to use non-specific binding in immunoassays. Particularly, where the assay involves an antigen or antibody immobilized on a solid substrate it is desirable to minimize the amount of non-specific binding to the substrate. Means of using such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

4. Labels.

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, Texas red, rhodamine, and the like), radiolabels (e.g., $^{3}H$, $_{125}I$, $_{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Thyroxine, and cortisol can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

IV. Screening for Modulators of Breast Cancer

The invention also provides methods of identifying compounds that modulate tumorigenicity of a cell. For example, the methods can identify compounds that increase or decrease the expression level of genes associated with breast cancer and related conditions. Compounds that are identified as modulators of breast cancer using the methods of the invention find use both in vitro and in vivo. For example, one can treat cell cultures with the modulators in experiments designed to determine the mechanisms by which breast cancer is regulated. Compounds that decrease or delay tumorigenicity are useful for extending the useful life of cell cultures that are used for production of biological products such as recombinant proteins. In vivo uses of compounds that delay tumorigenicity would have therapeutic benefit.

The methods typically involve culturing a cell in the presence of a potential modulator to form a first cell culture. RNA from the first cell culture is contacted with a probe which comprises a polynucleotide sequence associated with breast cancer. The amount of the probe which hybridizes to the RNA from said first cell culture is determined. Typically, one determines whether the amount of probe which hybridizes to the RNA is increased or decreased relative to the amount of said probe which hybridizes to RNA from a second cell culture grown in the absence of the modulator.

Essentially any chemical compound can be used as a potential modulator in the assays of the invention, although most often compounds can be dissolved in aqueous or organic (for example, DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St.

Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential therapeutic compounds (potential modulator compounds). Such wcombinatorial chemical librariesv are then screened in one or more assays, as described herein, to identify those library members (particular chemical species or subclasses) that display a desired characteristic activity. The compounds thus identified can serve as conventional wleadcompoundsv or can themselves be used as potential or actual therapeutics.

A combinatorial chemical library is a collection of diverse chemical compounds generated by either chemical synthesis or biological synthesis, by combining a number of chemical wbuildingblocksv such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with t-D-glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

As noted, the invention provides in vitro assays for identifying, in a high throughput format, compounds that can modulate cell tumorigenicity. Control reactions that measure the tumorigenicity of the cell in a reaction that does not include a potential modulator are optional, as the assays are highly uniform. Such optional control reactions are appropriate and increase the reliability of the assay. Accordingly, in a preferred embodiment, the methods of the invention include such a control reaction. For each of the assay formats described, wnomodulatorv control reactions which do not include a modulator provide a background level of binding activity.

In some assays it will be desirable to have positive controls to ensure that the components of the assays are working properly. At least two types of positive controls are appropriate. First, a known activator of cell tumorigenicity can be incubated with one sample of the assay, and the resulting increase in signal resulting from an increased expression level of a gene associated with breast cancer determined according to the methods herein. Second, a known inhibitor of tumorigenicity can be added, and the resulting decrease in tumorigenicity similarly detected. It will be appreciated that modulators can also be combined with activators or inhibitors to find modulators which inhibit the increase or decrease that is otherwise caused by the presence of the known modulator of cell tumorigenicity.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (96) modulators. If 1536 well plates are used, then a single plate can easily assay from about 100-about 1500 different compounds. It is possible to assay many different plates per day; assay screens for up to about 6,000–20,000, and even up to about 100,000 different compounds is possible using the integrated systems of the invention.

V. Diagnostic Kits

Diagnostic kits that include one of the components described above for the specific detection of overexpression of the breast cancer-associated proteins described herein, together with instructions for detection of such protein are contemplated. For example, a vial containing antibodies specific for the BCAS protein or nucleic acid homologous to or capable of specifically hybridizing to BCAS sequence can be included.

The invention provides compositions, kits and integrated systems for practicing the assays described herein. For example, an assay composition having a nucleic acid associated with tumorigenicity of a cell and a labelling reagent is provided by the present invention. In preferred embodiments, a plurality of BCAS nucleic acids are provided in the assay compositions. The invention also provides assay compositions for use in solid phase assays; such compositions can include, for example, one or more BCAS nucleic acids immobilized on a solid support, and a labelling reagent. In each case, the assay compositions can also include additional reagents that are desirable for hybridization. Modulators of expression of BCAS nucleic acids can also be included in the assay compositions.

The invention also provides kits for carrying out the assays of the invention. The kits typically include a probe which comprises a polynucleotide sequence associated with breast cancer; and a label for detecting the presence of said probe. Preferably, the kits will include a plurality of polynucleotide sequences associated with breast cancer. Kits can include any of the compositions noted above, and optionally further include additional components such as instructions to practice a high-throughput method of assaying for an effect on tumorigenicity and expression of BCAS genes, one or more containers or compartments (e.g., to hold the probe, labels, or the like), a control modulator of tumorigenicity, a robotic armature for mixing kit components or the like.

The invention also provides integrated systems for high-throughput screening of potential modulators for an effect on cell tumorigenicity. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip- compatible DOS™, OS2™, WINDOWS™, WINDOWS NT™, or WINDOWS95™ based computers), MACINTOSH™, or UNIX based (e.g., SUN™ work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VI. Screening Assays for Pharmaceutical Agents of Interest Useful to Block the Production of a BCAS Protein.

Since the overexpression of the BCAS is implicated in breast cancer, assays directed to identifying potential pharmaceutical agents that inhibit the activity of any of these proteins or their expression will be useful in determining the impact on tumor cell growth and proliferation of such agents and provide an indication of therapeutic potential for the agents in this disease. The assay could determine whether expression of the protein is limited or, more preferably, whether tumor cell growth is inhibited or stopped. Further, assays may alternatively be directed to screening agents that have potential for inhibiting tumor cell growth by exploiting the overexpression of the BCAS protein of interest. These assays would primarily determine whether the tumor cell growth is inhibited or not.

Such assays comprise incubating a compound to be evaluated for use in breast cancer treatment with breast cancer cells that overexpress such protein and determining therefrom the effect of the compound on the activity of such agent. In vitro assays in which the protein is overexpressed in suitable cell culture are preferred, though in vivo animal models would also be effective. Once an agent is found to be of interest in vitro, it would be screened similarly in an in vivo animal model.

VII. Inhibitory Nucleic Acids

Also contemplated here are inhibitory nucleic acid therapeutics which can inhibit tumor cell growth and which are directed to any of the BCAS gene sequences of interest. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid (the gene in FIG. 1 or copies of it), the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of, for example, one of the BCAS genes. These different types of inhibitory nucleic acid technology are described in Helene, C. and Toulme, J., 1990, *Biochim. Biophys. Acta*. 1049:99–125, for example, which is hereby incorporated by reference and is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al., 1988, *PNAS (USA)* 85:1028–1032 and Harel-Bellan, A., etal., 1988, *Exp. Med*. 168:2309–2318. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

VIII. Gene Therapy

A variety of human diseases may be treated by therapeutic approaches that involve stably introducing a gene into a human cell such that the gene may be transcribed and the gene product may be produced in the cell. Diseases amenable to treatment by this approach include inherited diseases where the defect is with a single gene. For discussions on the application of gene therapy towards the treatment of genetic as well as acquired diseases. See Miller, A. D. (1992) *Nature* 357:455–460, and Mulligan, R. C. (1993) *Science* 260:926–932, both incorporated herein by reference.

Delivery of the gene or genetic material into the cell is the first critical step in gene therapy treatment of disease. In this case, the goal would be to disrupt the expression of the BCAS gene of interest in the target cells. A variety of methods have been used experimentally. Most research has focused on the use of retroviral and adenoviral vectors for gene delivery into the cell. Retroviral vectors have the ability to stably integrate the transferred gene sequences into the chromosomal DNA of the target cell. Retroviral vectors are particularly attractive because they are very efficient in stably transducing a high percentage of target cells. Accordingly most of the approved gene therapy clinical protocols use retroviral vectors. See Miller, A. D., (1992) supra.

Retroviral vectors are particularly useful for modifying cells because of the high efficiency with which the retroviral vectors transduce target cells and integrate into the target cell genome. Additionally, the retroviruses harboring the retroviral vector are capable of infecting cells from a wide variety of tissues.

Retroviral vectors are produced by genetically manipulating retroviruses. Retroviruses are called RNA viruses because the viral genome is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R. C., In: *Experimental Manipulation of Gene Expression*, M. Inouye (ed), 155–173 (1983); Mann, R., et al., *Cell*, 33:153–159 (1983); Cone, R. D. and R. C. Mulligan, *Proceedings of the National Academy of Sciences, U.S.A.*, 81:6349–6353 (1984).

The design of retroviral vectors is well known to one of skill in the art. See Singer, M. and Berg, P. supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa, *Biotechniques* 4:504–512 (1986), Mann, et al., *Cell* 33:153–159 (1983), Cone and Mulligan, *Proc. Natl. Acad. Sci. USA* 81:6349–6353 (1984), Eglitis, M.A, et al. (1988) *Biotechniques* 6:608–614, Miller, A. D. et al. (1989) *Biotechniques* 7:981–990, Miller, A. D.(1992) *Nature*, supra, Mulligan, R. C. (1993), supra. and Gould, B. et al., and International Patent Application No. WO 92/07943 entitled "Retroviral Vectors Useful in Gene Therapy". The teachings of these patents and publications are incorporated herein by reference.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell and is capable of integrating into the host cell genome as a proviral sequence containing the desired nucleotide sequence. As a result, the patient is capable of producing target protein and thus restore the cells to a normal, non-cancerous phenotype.

Packaging cell lines are used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13. See Miller et al., *J. Virol.* 65:2220–2224 (1991), which is incorporated herein by reference. Examples of other packaging cell lines are described in Cone, R. and Mulligan, R. C., *Proceedings of the National Academy of Sciences, USA*, 81:6349–6353 (1984) and in Danos, O. and R. C. Mulligan, *Proceedings of the National Academy of Sciences, USA*, 85:6460–6464 (1988), Eglitis, M. A., et al. (1988) supra and Miller, A. D., (1990) supra, also all incorporated herein by reference. Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

The gene therapy vectors can be administered directly to the organism for transduction of cells in vivo. Administration can be by any of the routes normally used for introducing virus into ultimate contact with blood or tissue cells. The viral vectors used in the present inventive method are administered in any suitable manner, preferably with pharmaceutically acceptable carriers. Suitable methods of administering such viral vectors in the context of the present invention to a patient are available, and, although more than one route can be used to administer a particular viral vector, a particular route can often provide a more immediate and more effective reaction than another route.

Pharmaceutically acceptable carriers are determined in part by the particular viral vector being administered, as well as by the particular method used to administer the composition. Accordingly, there is a wide variety of suitable formulations of the pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the viral vector, carriers known in the art.

The viral vector, alone or in combination with other suitable components, can be made into aerosol formulations to be administered via inhalation. Because the bronchial passageways are the usual route of choice for certain viruses, corresponding vectors are appropriately administered by this method. Aerosol formulations can be placed into pressurized acceptable propellants, such as dichlorodifluoromethane, propane, nitrogen, and the like.

Suitable formulations for rectal administration include, for example, suppositories, which consist of the active viral vector with a suppository base. Suitable suppository bases include natural or synthetic triglycerides or paraffin hydrocarbons. In addition, it is also possible to use gelatin rectal capsules which consist of a combination of the viral vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, intrathecal (in the cerebrospinal fluid), and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a patient, in the context of the present invention should be sufficient to effect a beneficial therapeutic response in the patient over time. The dose will be determined by the efficacy of the particular viral vector employed and the condition of the patient or animal, as well as the body weight or surface area of the patient to be treated. The size of the dose also will be determined by the existence, nature, and extent of any adverse side-effects that accompany the administration of a particular vector or transduced cell type in a particular patient or animal.

In determining the effective amount of the viral vector to be administered in the treatment or prophylaxis of a particular disease, the physician or veterinarian needs to evaluate circulating plasma levels, vector toxicities, and progression of the disease.

In the practice of this invention, the vectors can be administered, for example, by aerosolization and inhalation, intravenous infusion, orally, topically, intramuscularly, intraperitoneally, intravesically or intrathecally. The preferred method of administration will often be intravenous or by inhalation, but the vector can be applied in a suitable vehicle for the local and topical treatment of virally-mediated conditions.

For administration, vector and transduced cell types of the present invention can be administered at a rate determined by the $LD_{50}$ of the particular vector, and the side-effects of the vector or cell type at various concentrations, as applied to the mass and overall health of the patient. Administration can be accomplished via single or divided doses.

Protocols for in vivo gene therapy using adeno-associated viral vectors have been described for the brain (Alexander et al. (1996) *Human Gene Ther.* 7: 841–850), liver (Koeberl et al. (1997) *Proc. Nattl. Acad. Sci. USA* 94: 1426–1431), lung (Flotte etal. (1993) *Proc. Nattl. Acad. Sci. USA* 90: 10613–10617), and muscle (Xiao et al. (1996) *J. Virol.* 70: 8098–8108). These methods can be adapted to other target organs by those of skill in the art.

IX. Antibody and Small Molecule Blocking of Expression

Treatments for inhibiting tumor cell growth can be employed based on the association herein by administering antibodies or other specifically reactive molecules with a BCAS protein of interest which block the activity of the protein. Such immunoreactive molecules can be made as described above.

X. Administration of Pharmaceutical Compositions

The antibody and other pharmaceutical compositions for inhibiting tumor cell growth are preferably administered to mammals via oral, intravenous or parenteral administrations and other systemic forms, particularly where the disease is metastatic. In the case of primary disease, administration may be more localized to the diseased area. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

The pharmaceutical composition may be administered to a patient either singly or in a cocktail containing two or more antibodies, other therapeutic agents, compositions, or the like, including, but not limited to, immunosuppressive agents, potentiators and side-effect relieving agents. Of particular interest are immunosuppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference*, 41st Ed. (1 987), Publisher Edward R. Barnhart, New Jersey.

The composition may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized antibody compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies will be administered in a therapeutically effective dose in a range of from about 0.01 mg/kg to about 5 mg/kg of the treated mammal. A preferred therapeutically effective dose of the pharmaceutical composition containing antibody will be in a range of from about 0.01 mg/kg to about 0.5 mg/kg body weight of the treated mammal administered over several days to two weeks by daily intravenous infusion, each given over a one hour period, in a sequential patient dose-escalation regimen.

The compositions may be administered systemically by injection i.m., subcutaneously, intrathecally or intraperitoneally or into vascular spaces, particularly into the joints, e.g., intraarticular injection at a dosage of greater than about 0.001 $\mu$M joint fluid/day. The dose will be dependent upon the properties of the agent employed, e.g., its activity and biological half-life, the concentration of agent in the formulation, the site and rate of dosage, the clinical tolerance of the patient involved, the disease afflicting the patient and the like as is well within the skill of the physician.

The pharmaceutical composition of the present invention may be administered in solution. The pH of the solution should be in the range of pH 5 to 9.5, preferably pH 6.5 to 7.5. The antibody or other agent should be in a solution having a suitable pharmaceutically acceptable buffer such as phosphate, tris (hydroxymethyl) aminomethane-HCI or citrate and the like. Buffer concentrations should be in the range of 1 to 100 mM. The pharmaceutical composition may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or other agent or to the composition from which the solution is prepared. Antibody or other agent may also be administered via microspheres, liposomes or other microparticulate delivery systems placed in certain tissues including blood.

Dosages

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to inhibit or stop tumor cell growth without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

All publications and patent applications cited in this specification are herein incorporated by reference as if each individual publication or patent application were specifically and individually indicated to be incorporated by reference.

EXAMPLES

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for the detection of breast cancer in a cell population comprising breast cells suspected of being cancerous, the method comprising analyzing at least one breast cell to determine if the breast cell overexpresses a protein that specifically binds to polyclonal antibodies raised against a protein encoded by SEQ ID NO:5, wherein overexpression of the protein in said breast cell as compared to normal breast cells is an indicator of breast cancer.

2. The method of claim 1, wherein the cell is analyzed by quantitation of the protein.

3. The method of claim 1, wherein the breast cell is a human cell.

4. A method for detecting the presence of breast cancer in human tissue said method comprising:

(i) isolating a biological sample comprising breast cells from a human being tested for breast cancer, (ii) contacting the biological sample with an antibody which selectively binds to a protein encoded by SEQ ID NO:5; and (iii) detecting the existence of overexpression of a protein encoded by a nucleic acid sequence that encodes a protein that specifically binds to polyclonal antibodies raised against a protein encoded by SEQ ID NO:5 wherein overexpression of the protein in said breast cells as compared to normal breast cells is an indicator of breast cancer.

5. The method of claim 4, wherein the antibody is a monoclonal antibody.

6. The method of claim 4, wherein the antibody is a polyclonal antibody.

7. The method of claim 2, wherein quantitation of the protein is by immunoassay.

* * * * *

SEQUENCE LISTING

```
<160> NUMBER OF SEQ ID NOS: 5

<210> SEQ ID NO 1
<211> LENGTH: 384
<212> TYPE: DNA
<213> ORGANISM: Homo sapiens
<220> FEATURE:
<223> OTHER INFORMATION: Unidentified, GenBank Accession No. R17530
<221> NAME/KEY: modified_base
<222> LOCATION: (1)..(384)
<223> OTHER INFORMATION: n = g, a, c or t

<400> SEQUENCE: 1

gtgtgggacc cgctgctgat cctgtcgcag atcgtcctca tgcagaccgt gtattacggc     60

tcgctgggcc tgtggtggcg ctggtggacg ggctagtgcg aangcnccct cgctggacca    120

gatgttcgac gccgagatcc tgggcttttc cacccctcca ggccggctct ccatgatgtc    180

cttcatcctc aacgccctca cctgggagct gacatggacc caaatcctcg ggccgccctg    240

ggagcgccan aggcttccgc cttcgggagc ggcaaaaatt tttcgaggac atttttacag    300

ccagagacag agtttttttt ttcctctgtt cccatcttgc atctngaatt cgcaaaagaa    360

cccccataag gtagntattt tcaa                                           384


<210> SEQ ID NO 2
<211> LENGTH: 529
<212> TYPE: DNA
<213> ORGANISM: Homo sapiens
<220> FEATURE:
<223> OTHER INFORMATION: Unidentified, GenBank Accession No. R61133
<221> NAME/KEY: modified_base
<222> LOCATION: (1)..(529)
<223> OTHER INFORMATION: n = g, a, c or t

<400> SEQUENCE: 2

cagtcacagt ggaagaatgc atctgagaat gatgagcgct tatctaaccc ccagattgag     60

tggcagaata gcacaattga cagtgaggat ggggaacagt ttgacaacat gactgatgga    120

gtagctgagc ccatgcatgg cagcttagcc ggagttaaac tgagcagcca acaggcctaa    180

gtgccaggtt ccctggcgtt ggtgacatgc tgcagcctgg aactctgatc tccagtgtga    240

ctgcaaagct gtcttctcac tggtactgcc ttgtgagtac tggttggact gtggggcatg    300

tggccgctgc agttccagtg gttatttcta agtctatgac aggacaggct gttcttgctt    360

cagaaccttc tctgacagac acggtaacta aatgttgaaa aaccaataag ctggtgantc    420

attgaataca cacgagggaa aagcagaggt tttntttatt ctggcctttt caacattttt    480

ttcccccngt ggaaattgat tggtcagatg tcttttgagn agtgtttaa                529


<210> SEQ ID NO 3
<211> LENGTH: 405
<212> TYPE: DNA
<213> ORGANISM: Homo sapiens
<220> FEATURE:
<223> OTHER INFORMATION: HsCdc18p, GenBank Accession No. T83032
<221> NAME/KEY: modified_base
<222> LOCATION: (1)..(405)
<223> OTHER INFORMATION: n = g, a, c or t

<400> SEQUENCE: 3

nttcggcacg gagaaccaac aaatgtccaa accgtaacct gttctcctcg tgtaaaagcc     60

ctgcctctca gccccaggaa acgtctgggc gatgacaacc tatgcaacac tccccattta    120
```

-continued

```
cctccttgtt ctccaccaaa gcaaggcaag aaagagaatg gtccccctca ctcacataca    180

cttaagggac gaagattggt atttgacaat cagctgacaa ttaagtctcc tagcaaaaga    240

gaactagcca aagttcacca aaacaaaata ctttcttcag ttagaaaaag tcaagagatt    300

cacaacaaat tctgaggcag agatgtccac tgganggatt tatctggctg tgtggggatt    360

tttcaggcag gagggcattg nttaccagca ggcaaagtgg gttcc                     405
```

```
<210> SEQ ID NO 4
<211> LENGTH: 483
<212> TYPE: DNA
<213> ORGANISM: Homo sapiens
<220> FEATURE:
<223> OTHER INFORMATION: human chorionic gonadotropin, GenBank Accession
      No. H00694
<221> NAME/KEY: modified_base
<222> LOCATION: (1)..(483)
<223> OTHER INFORMATION: n = g, a, c or t

<400> SEQUENCE: 4

nctttatttg cagtggaaca agctaaatgc tgtattcatt ccaaatgaaa agaactagac     60

tgctgattgt actgtaggat aaggaggaag gcagtaaagc tgcagtatat ccttgaagcg    120

tgtcaaagtg gtatggtaag gaaaaggaga gttttatctc acaaagccat aaacactaaa    180

caacttaatt ttccattcca gaaaatcagc agtcatcaag acagcacttg ggtaaaacat    240

ttaagatttg tgataataac aagtactgca gtggcacgcc gtgtgggttc tccactttga    300

aaccccccat tactgtgacc ctgttatatg atttaggcta cacagcaagt gggactctga    360

gggtgacgtt cttttgggac caacatcgtc ttcttgggac cntagtggga gtggggtatg    420

gctctagggg aggcaggcag ccccatgcac tngaagtatt ngggcaccc ggctngggag     480

ntt                                                                  483
```

```
<210> SEQ ID NO 5
<211> LENGTH: 636
<212> TYPE: DNA
<213> ORGANISM: Homo sapiens
<220> FEATURE:
<223> OTHER INFORMATION: human 14-3-3 protein eta chain, GenBank
      Accession No. AA256774

<400> SEQUENCE: 5

aagaaattgg agaaagttaa agcttaccgg gagaagattg agaaggagct ggagacagtt     60

tgcaatgatg tcctgtctct gcttgacaag ttcctgatca agaactgcaa tgatttccag    120

tatgagagca aggtgtttta cctgaaaatg aagggtgatt actaccgcta cttagcagag    180

gtcgcttctg ggagaagaa aaacagtgtg gtcgaagctt ctgaagctgc ctacaaggaa    240

gcctttgaaa tcagcaaaga gcagatgcaa cccacgcatc ccatccggct gggcctggcc    300

ctcaacttct ccgtgttcta ctatgagatc cagaatgcac ctgagcaagc ctgcctctta    360

gccaaacaag ccttcgatga tgccatagct gagctggaca cactaaacga ggattcctat    420

aaggactcca cgctgatcat gcagttgctg cgagacaacc tcaccctctg gacgagcgac    480

ccgcaggatt gaagaagcag aagaaggcca ctgaagatct ttcaggtccc ctggcccttc    540

cttcacccac cacccccatc atcaacgatt cttccttgcc acaatcacta aatatctagt    600

gctaaaccta tctgtattgg cagcacagct actcag                             636
```